United States Patent
Nakayama et al.

[11] Patent Number: 5,384,258
[45] Date of Patent: Jan. 24, 1995

[54] BACILLUS STEAROTHERMOPHILUS AND E. COLI PLASMIDS

[75] Inventors: Noriyuki Nakayama; Shinya Nakamoto, both of Tokyo, Japan

[73] Assignee: NEC Corporation, Japan

[21] Appl. No.: 148,988

[22] Filed: Nov. 8, 1993

[30] Foreign Application Priority Data

Dec. 24, 1992 [JP] Japan .................................. 4-343721
Mar. 26, 1993 [JP] Japan .................................. 5-067261

[51] Int. Cl.6 ........................ C12N 15/75; C12N 15/00
[52] U.S. Cl. ................................................. 435/320.1
[58] Field of Search ...................................... 435/320.1

[56] References Cited
PUBLICATIONS

Gene Technology, pp. 134–167, Kyouritu Shuppan K.K., 1987.
H. Liao et al., Proc. Natl. Acad. Sci. USA, vol. 83, pp. 576–580.
Biotechnology Techniques, vol. 6, No. 1, 83–36 (1992).

Primary Examiner—Richard A. Schwartz
Assistant Examiner—Gary L. Brown
Attorney, Agent, or Firm—Laff, Whitesel, Conte & Saret, Ltd.

[57] ABSTRACT

A plasmid pSTK1 having about 1880 bp and the restriction map set forth in FIG. 1 and plasmids pSTE33 and PSTK3 derived therefrom. The plasmids are capable of stable replication in thermophilic bacteria.

7 Claims, 2 Drawing Sheets

BACILLUS STEAROTHERMOPHILUS AND E. COLI PLASMIDS

BACKGROUND OF THE INVENTION

1. Field of the Invention

This invention relates to plasmids being capable of being replicated in thermophilic bacteria and in particular plasmids being capable of stably being replicated in grampositive thermophilic bacteria which grow at high temperature.

2. Description of the Related Art

As for plasmids which are capable of being replicated in thermophilic bacteria, particularly thermophilic bacteria of genus Bacillus, some plasmids such as pUB110, pIH41 and the like have been reported. However, these plasmids which were introduced in a host have been more frequently lost from the host when the host with the plasmids was incubated at a temperature of 60° C. or more without applying selection pressure due to addition of antibiotic substances (for example, "Gene Technology" edited by T. Andou et al., pp. 134–167, Kyouritu Shuppan K. K., 1987), the disclosure of which is hereby incorporated by reference herein.

The above-mentioned plasmids encode resistance factors against antibiotic substances such as kanamycin or the like. For this reason, by incubating the plasmid-bearing bacterium in a culture medium containing the corresponding antibiotic substance, it is possible to selectively kill the host from which the plasmids were lost and to grow only the plasmid-bearing host, whereby the loss of the plasmids can be apparently prevented. However, in addition to the cost for the antibiotic substance usage, treatment of the residual antibiotic substance in the culture medium after incubation is very expensive. Thus, mass incubation of the plasmid-bearing bacteria requires great deal of expense.

SUMMARY OF THE INVENTION

Accordingly, an object of this invention is to obviate the above-mentioned problems and thus to provide a plasmid which is stably borne in a host.

According to a first embodiment of this invention, there is provided a plasmid pSTK1 having about 1880 bp and the restriction map set forth in FIG. 1.

According to a second embodiment of this invention, there is provided a plasmid pSTE33 having about 5650 bp and the restriction map set forth in FIG. 1.

According to a third embodiment of this invention, there is provided a plasmid pSTK3 having about 3020 bp and the restriction map set forth in FIG. 2.

The foregoing and other objects and features of this invention will be apparent from the following description.

DETAILED DESCRIPTION OF THE PREFERRED EMBODIMENTS

This invention will be hereinafter described in more detail with reference to the following non-limiting working

EXAMPLES

1. Obtainability of plasmid pSTK1

Figure 1:
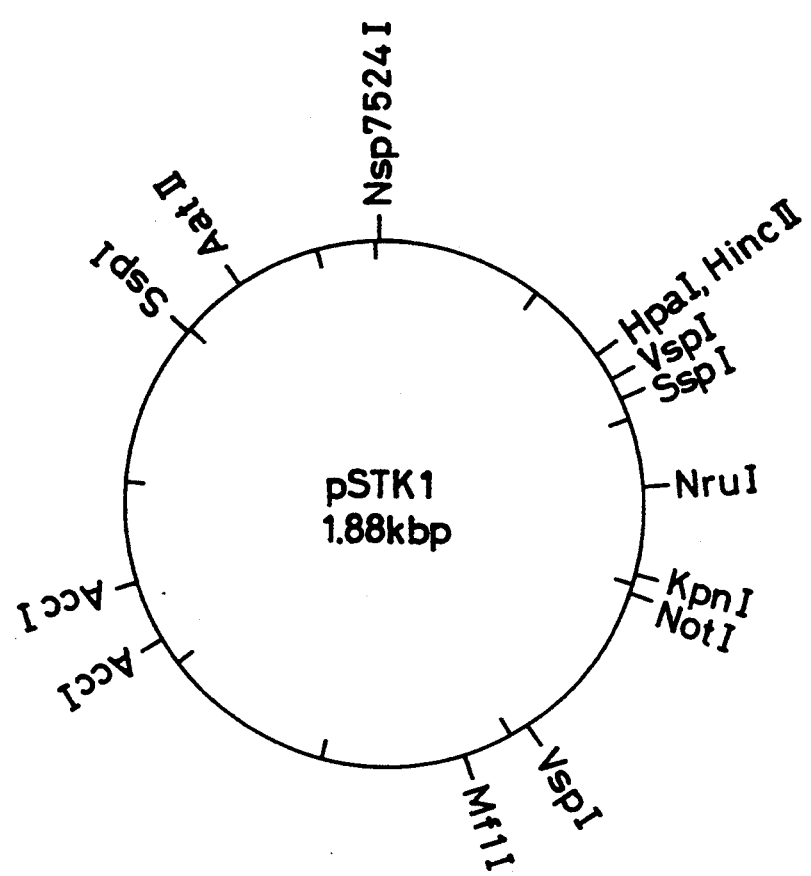
FIG. 1 shows a restriction map of a plasmid pSTK1 according to this invention.

A sample taken or harvested from soil was inoculated on 5 ml of an MG medium (0.5% of glucose, 0.02% of nitrilotriacetic acid, 0.052% of dipotassium hydrogenphosphate, 0.015% of potassium dihydrogenphosphate, 0.015% of magnesium sulfate.7 hydrates, 0.013% of calcium chloride.2 hydrates and 0.05% of sodium nitrate, at pH 7.2) and was incubated overnight at 70° C. The culture medium (100 μl) was spread on an MG-agar plate (2.0 wt. % of agar was added to the MG medium) and incubated for one day. Colonies on plate were picked up and were subjected to purification. Thereafter, the isolates were subjected to shaking culture overnight at 70° C. in 5 ml of an L medium (1% of trypton, 0.5% of yeast extract and 0.5% of NaCl, at pH 7.2) and then plasmid DNA's were extracted by a conventional method such as an alkaline lysis method. The extract was subjected to ethanol sedimentation and recovered under centrifugation, and then subjected to an agarose gel electrophoresis to confirm the presence and absence of plasmids. The above-mentioned procedures were repeated with respect to each of a number of isolated strains to select plasmid-bearing strains. Three kinds of plasmids were found in a *Bacillus stearothermophilus* TKO15 strain and the plasmid having the lowest molecular weight among them was named pSTK1. A restriction map of the plasmid pSTK1 is shown in FIG. 1.

The *B. stearothermophilus* TKO15 strain bearing plasmid pSTK1 was deposited with the National Institute of Bioscience and Human-Technology Agency of Industrial Science and Technology which corresponds to the International Depository Authority, of 1-3, Higashi 1 chome, Tsukuba-shi, Ibaraki-ken, 305, Japan, on Mar. 12, 1993, under deposit number FERM BP-4449, according to the Budapest Treaty on the International Recognition of the Deposit of Microorganisms for the purposes of Patent Procedure.

2. Construction of plasmids pSTE33 and pSTK3

Figure 2:
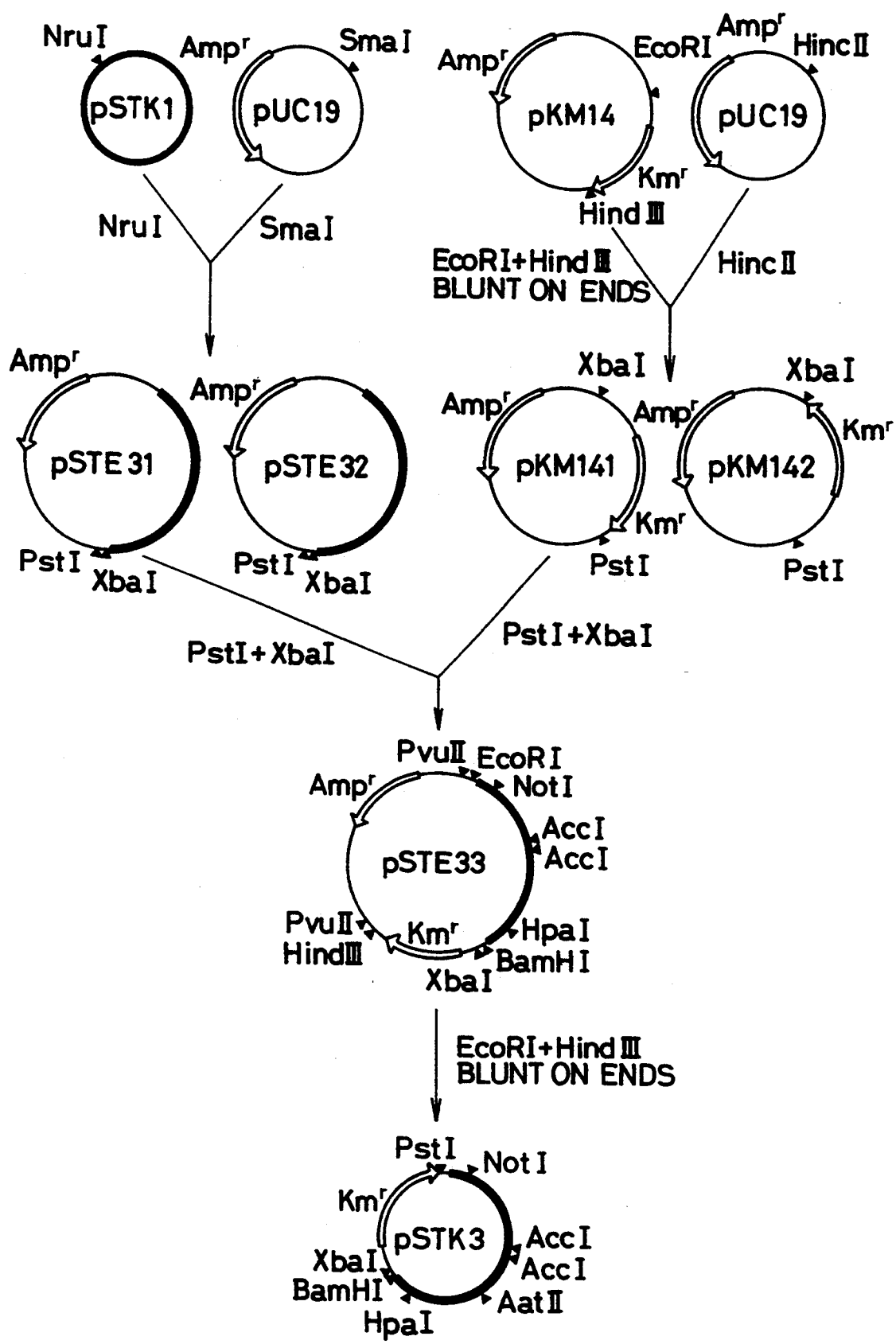
FIG. 2 is a scheme of construction of plasmids pSTE33 and pSTK3 according to this invention.

Scheme of construction of plasmids pSTE33 and pSTK3 will be described with reference to FIG. 2.

(1) After plasmid pUC19 (trade name, manufactured by TAKARA SHUZO CO., LTD.) was completely digested with a restriction endonuclease SmaI, it was purified by means of phenol extraction. Alkaline phosphatase acted on the purified plasmid to remove phosphate groups at 5' end. To the resulting plasmid, was added plasmid pSTK1 which was cleaved and linearized with a restriction endonuclease NruI, and both of the plasmids were ligated with T4 DNA ligase to thus be circulized into a reaction product.

*Escherichia coli* JM109 strain was transformed with the above reaction product to ampicillin resistance transformants, from which plasmids were extracted according to a conventional method. It was confirmed by electrophoresis that from a cleavage pattern due to restriction endonucleases, the resulting plasmids consist of two plasmids of pSTE31 and pSTE32 which are different in direction of a pSTK1 fragment inserted therein and each of which has a size of about 4.6 kbp.

(2) Plasmid pKM14 (which is held by Jichi Medical School, School of Nursing, H. Kihara) was completely digested with restriction endonucleases EcoRI and HindIII to give a DNA fragment having about 1.1 kbp and carrying a kanamycin resistance gene. Both ends of the fragment were blunted with T4 DNA polymerase and then inserted into and ligated to a site of a restriction endonuclease HincII of plasmid pUC19 to give a reaction product. *E. coli* JM109 strain was transformed with the reaction product to ampicillin resistance transformants, from which plasmids were extracted according to the conventional method. It was confirmed by electrophoresis that from a cleavage pattern due to restriction endonucleases, the resulting plasmids consist of two plasmids of pKM141 and pKM142 which are different in insertion direction of a DNA fragment carrying the kanamycin resistance gene and each of which has a size of about 3.8 kbp.

The above-mentioned plasmid pKM141 was constructed as follows. A kanamycin resistant gene carried on plasmid pUB110(trade name, manufactured by Sigma Chemical Company) was modified to a thermostable kanamycin resistant gene by means of evolutionary engineering as shown in H. Liao et al., Proc. Natl. Acad. Sci. USA, Vol. 83, pp. 576–580, February 1986, the disclosure of which is hereby incorporated by reference herein. The thermostable kanamycin resistant gene was introduced into plasmid pUC18 (trade name, manufactured by TAKARA SHUZO CO., LTD.) to construct plasmid pUC-TK101 (about 4.2 kbp). Then, a pUB110 fragment carrying the thermostable kanamycin resistant gene on plasmid pUC-TK101 was digested with exonuclease Bal31, and thereafter was introduced into plasmid pUC118 (trade name, manufactured by TAKARA SHUZO CO., LTD.) to construct plasmid pKM14 (about 4.2 kbp).

(3) Plasmid pKM141 was completely digested with restriction endonucleases XbaI and PstI to give a DNA fragment having about 1.1 kbp and carrying a kanamycin resistance gene. The resulting DNA fragment was ligated to a DNA fragment of about 4.6 kbp, which was prepared by completely digesting the plasmid pSTE31 with restriction endonucleases XbaI and PstI, with T4 DNA ligase to give a reaction product. *E. coli* JM109 strain was transformed with the above reaction product to ampicillin resistance transformants, from which plasmids were extracted according to the conventional method. The plasmid thus extracted has a size of about 5650 bp and is named pSTE33.

The *E. coli* JM109 strain bearing plasmid pSTE33 was deposited with the above-mentioned depository authority on Mar. 12, 1993, under deposit number FERM BP 4451.

(4) Plasmid pSTE33 was completely digested with restriction endonucleases EcoRI and HindIII to give a DNA fragment of about 3020 bp. Both ends of the fragment were blunted with T4 DNA polymerase and thereafter ligated with T4 DNA ligase to give a circulized reaction product. *B. stearothermophilus* K1041 strain was transformed with the reaction product. The transformation was performed by an electroporation method as shown in Biotechnology Techniques, Vol. 6, No. 1, 83–86 (1992), the disclosure of which is hereby incorporated by reference herein. Bacteria treated by the electroporation method were spread on L agar plates (2.0 wt. % of agar was added to an L medium and solidified) containing 10 μg/ml of kanamycin and incubated at 48° C. for 24 hours to give kanamycin resistance transformants, from which plasmids were extracted by the conventional method. The plasmid thus extracted has a size of about 3020 bp and was named pSTK3.

*B. stearothermophilus* K1041 strain bearing plasmid pSTK3 was deposited with the above-mentioned depository authority on Mar. 12, 1993 under deposit number, FERM BP 4450.

3. Stability of plasmids pSTE33 and pSTK3:

*B. stearothermophilus* K1041 strain was transformed with each of the plasmids pSTE33 and pSTK3 in the same manner as mentioned above. The resulting transformants were subjected to shaking culture of about 20 generations at 60° C. in L medium and thereafter cultures appropriately diluted were spread on L agar plates and the L agar plates containing 10 μg/ml of kanamycin and incubated at 48° C. for 24 hours, and thereafter the number of colonies formed on both of the agar plates was compared. The same procedures were repeated at different temperatures in L medium at 47, 57 and 67° C.

From the above comparative data, it was determined that in all of the transformants, the colonies of approximately the same number were formed on the both agar plates independing on the culture temperature.

As for the plasmid pSTE33, all the DNA's were extracted from the incubated bacteria at each of the above-mentioned temperatures and were subjected to an electrophoresis. Then the number of copies of the plasmid was calculated from the ratio of chromosome DNA and plasmid DNA, with the results that the number of the copies did not change at temperatures ranging from 47°–67° C.

4. Versatility of drug resistance gene:

Transformation of *E. coli* JM109 was performed by utilizing the kanamycin resistance gene introduced into each of the plasmids pSTE33 and pSTK3. As for the plasmid pSTE33, the transformation efficiency of *E. coli* was about $10^5$ CFU/μg whereas as for the plasmid pSTK3, it was about $10^4$ CFU/μg. From this result, it is seen that not only the plasmid pSTE33 but also the plasmid pSTK3 serve as a shuttle vector between the *E. coli* and the thermophilic bacteria.

As discussed above, the plasmids pSTE33 and pSTK3 according to this invention, which contain the restriction endonuclease NruI cut plasmid pSTK1, are stably maintained in the host organism even when the thermophilic bacteria of genus Bacillus such as *B. stearothermophilus* are transformed with each of the plasmids and then the transformants are incubated at 70° C. over about 20 generations. Therefore, even when the transformants are incubated at a high temperature, it is not necessary to add the antibiotic substance to the culture medium. This can easily lead to several technological applications utilizing the transformants.

It is apparent that the above-mentioned stability of the plasmids pSTE33 and pSTK3 is based on the function of the plasmid replication. Therefore, in addition to the plasmids pSTE33 and pSTK3 of this invention, it is to be appreciated that it is possible to construct several plasmids having the stability similar to that of the plasmids pSTE33 and pSTK3 by using all or part of DNA fragments of the plasmid pSTK1.

If *B. stearothermophilus* is used as a host, the plasmid pSTK1 does not let the host have the character as can be utilized as a marker but the plasmids pSTE33 and pSTK3 let the host have the kanamycin resistance.

Since the plasmid pSTE33 carries the DNA fragment derived from the plasmid pUC19, it can be replicated by using *E. coli* as a host. Therefore, if cloning, subcloning or the like of a target gene is performed using the *E. coli* which has higher transformation efficiency and well-known biological properties and thereafter the resulting recombinant plasmid is introduced into *B. stearothermo-*

*philus*, several technological applications can be sufficiently examined.

Although the plasmid pSTK3 is a plasmid prepared by removing a pUC19 region from the plasmid pSTE33 to shorten the pSTE33, it can utilize the *E. coli* as a host and has a smaller size of about 3020 bp. Therefore, it is possible to clone the target DNA fragment larger than that inserted into plasmid pSTE33.

While this invention has been described in connection with certain preferred embodiments, it is to be understood that the subject matter encompassed by way of this invention is not to be limited to those specific embodiments. On the contrary, it is intended for the subject matter of the invention to include all alternatives, modifications and equivalents as can be included within the spirit and scope of the following claims.

What is claimed is:

1. A plasmid pSTK1 having about 1880 bp and the restriction map set forth in FIG. 1.

2. A plasmid pSTE33 having about 5650 bp and the restriction map set forth in FIG. 2.

3. The plasmid pSTE33 as defined in claim 2, wherein said plasmid is a shuttle vector between *Escherichia coli* and thermophilic bacterium.

4. The plasmid pSTE33 as defined in claim 3, wherein said thermophilic bacterium is *Bacillus stearothermophilus*.

5. A plasmid pSTK3 having about 3020 bp and the restriction map set forth in FIG. 2.

6. The plasmid pSTK3 as defined in claim 5, wherein said plasmid is a shuttle vector between *Escherichia coli* and thermophilic bacterium.

7. The plasmid pSTK3 as defined in claim 6, wherein said thermophilic bacterium is *Bacillus stearothermophilus*.

* * * * *